US010638974B1

(12) United States Patent
Yang

(10) Patent No.: US 10,638,974 B1
(45) Date of Patent: May 5, 2020

(54) WEARABLE DEVICE

(71) Applicant: Thunder Power New Energy Vehicle Development Company Limited, Central (HK)

(72) Inventor: Fuchia Yang, Taipei (TW)

(*) Notice: Subject to any disclaimer, the term of this patent is extended or adjusted under 35 U.S.C. 154(b) by 0 days.

(21) Appl. No.: 16/219,889

(22) Filed: Dec. 13, 2018

(51) Int. Cl.
*G08B 1/08* (2006.01)
*A61B 5/00* (2006.01)
*A61B 5/01* (2006.01)
*A61B 5/08* (2006.01)

(52) U.S. Cl.
CPC .......... *A61B 5/6804* (2013.01); *A61B 5/0008* (2013.01); *A61B 5/01* (2013.01); *A61B 5/082* (2013.01)

(58) Field of Classification Search
CPC ......... A61B 5/6804; A61B 5/082; A61B 5/01; A61B 5/0008
USPC .................................................... 340/539.12
See application file for complete search history.

(56) References Cited

U.S. PATENT DOCUMENTS

2013/0324868 A1* 12/2013 Kaib .................... A61N 1/3937
600/510
2014/0106677 A1* 4/2014 Altman ................ H04B 1/3827
455/41.2

\* cited by examiner

*Primary Examiner* — Tanmay K Shah
(74) *Attorney, Agent, or Firm* — Kilpatrick Townsend & Stockton, LLP

(57) ABSTRACT

Embodiments provide a wearable device and a method for monitoring a person wearing the wearable device. The wearable device includes sensors configured to generate signal of the person, data transmission component, data analysis device, monitoring device, and positioning components. The data transmission component receives and transmits the signal to the data analysis device. The data analysis device generates a pattern of the person based on the signal, then compares the pattern with one or more predetermined normal patterns of the person. When determining that the person is functioning abnormally, the data analysis device generates and transmits the alert instruction to a monitoring device to generate a notification for notifying a care-giver that the person is functioning abnormally. The positioning components provide location information of the wearable device so that the care-giver can locate the person.

18 Claims, 10 Drawing Sheets

602

604

Continuous fever

606

Undulant:

608

Intermittent:

610

Irregular:

612

WEARABLE DEVICE

FIELD OF THE INVENTION

This invention relates generally to wearable device and system, and more particularly, to a wearable device and system to detect abnormal functioning of a living subject, such as a person or an animal.

BACKGROUND OF THE INVENTION

Parents are concerned with the health of their children and especially infants. Infants and young children are very susceptible to infections that could lead to severe problems. Since children at very young ages cannot tell the parent when and why they do not feel well, parents and medical personnel relay on breath or temperature monitoring as an early warning indicator.

Since the neck of an infant is not yet fully developed, bone and muscle strength in the infant's neck is typically not strong enough to support the infant's head. Numerous incidents have been found that incorrect breathing postures by an infant can cause bone or even brain damages to the infant, and in some severe instances even death of the infant. The aforementioned breathing danger due to an infant's incorrect breathing posture may become even more acute when a care-giver of the infant is not paying attention to the infant. Therefore there is a need to determine an incorrect breathing posture engaged in by an infant and notify the care-giver of such.

One important key to an infant's health is maintaining an infant's body temperature within a certain data range. A high body temperature beyond a certain data range may be undesirable. The third leading cause of death among infants 1 month to 1 year in age is Sudden Infant Death Syndrome (SIDS), the unexpected death of an infant typically under 1 year old, without explicable cause. While SIDS has no symptoms and provides no indication, parents can follow some precautionary measures to help minimize the possibility that their child may afflicted. One precautionary measure now being advocated by doctors is preventing a sleeping infant's body temperature from rising too high and/or too rapidly.

An abnormally low body temperature is equally undesirable. Because an infant contains less body fat than an adult, certain ambient temperatures that may be comfortable for an adult may be too cold for an infant. This would leave the infant uncomfortable which may lead to the infant crying and screaming. Furthermore, a low body temperature may also be indicative of a sickness.

Besides infant care, certain adults may need extended care to prevent hazards to their health. Typically, when hospitalized, adults may be given care through non-stop monitoring using hospital-grade equipment. However, hospital type of care is not possible while the adults are situated in home or long term care facilities. Nevertheless, non-stop monitoring of various vital signs such as breathing patterns, body temperature, heart rate, blood pressure, etc. is still very desirable even when those adults are not hospitalized.

BRIEF SUMMARY OF THE INVENTION

In one aspect, embodiments can provide a wearable device for monitoring a living subject, determining a living subject is breathing abnormally, having abnormal temperature, or having abnormal heartbeat or pulse, or having abnormal blood pressure, and/or any other health hazards; and automatically notifying the care-giver when the health hazards are detected. In various embodiments in accordance with the disclosure, a wearable device is provided for detecting and notifying of the health hazards.

In some embodiments, the wearable device may be configured to include a sound sensor that can collect breathing sounds by the person. For example, the wearable device may be attached to a collar of the clothing. In some embodiments, the wearable device may also include a wireless or wired data transmission component that can transmit the breathing sound signals collected by the sound sensors to a remote data analysis device. The remote data analysis device may be configured to process the sound signals and determine whether the person is breathing abnormally. When it is determined that the person is breathing abnormally, the remote data analysis device may be configured to generate an alert instruction. Such an instruction can be transmitted to a monitoring device to generate a notification for notifying a care-giver of the person that the person is breathing abnormally.

In some embodiments, the data analysis device is configured to generate an alert instruction after abnormal breathing by the person is detected. The alert instruction can be transmitted to a monitoring device associated with a care-giver of the person and may be implemented on the monitoring device to notify the care-giver of the abnormal breathing by the person. In some embodiments, the monitoring device associated with the care-giver can include a smart phone or a tablet device.

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and embodiments, will become more apparent upon referring to the following specification, claims, and accompanying drawings.

DETAILED DESCRIPTION OF THE INVENTION

Figure 1:
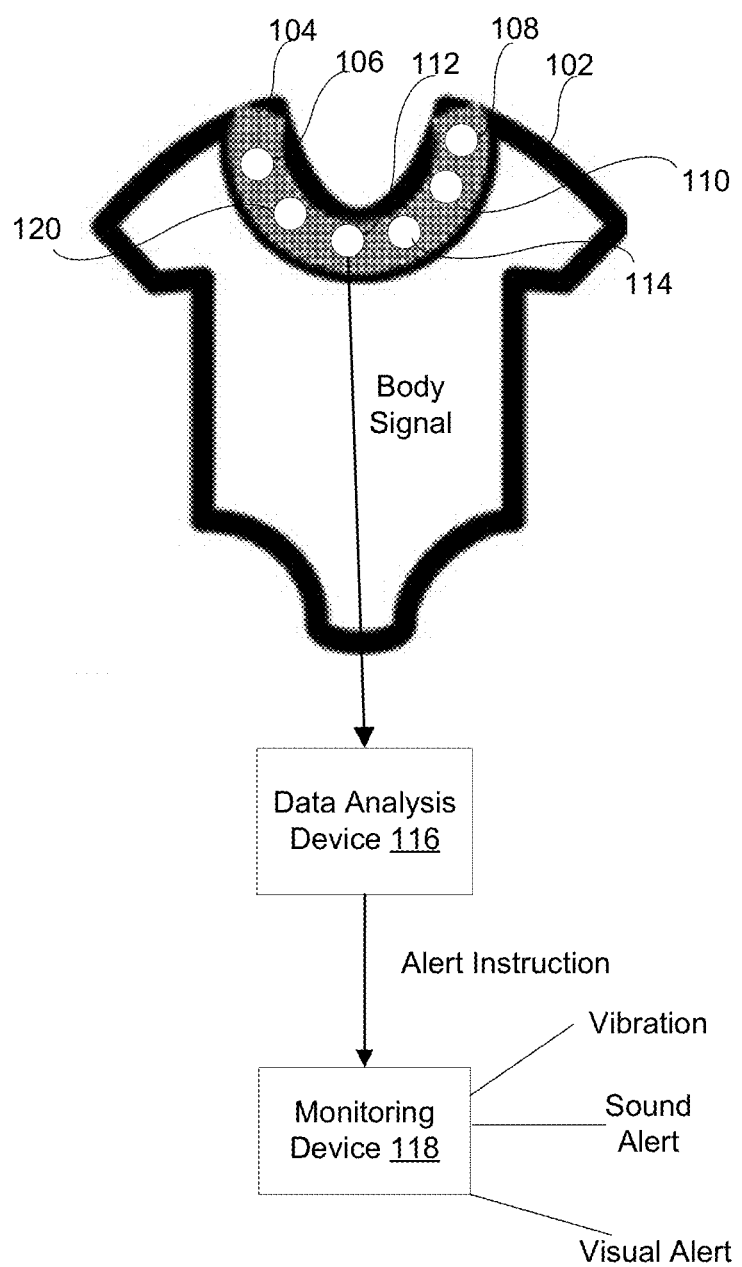
FIG. 1 illustrates one example of a wearable device that has a breathing sensor, a temperature sensor, a data transmission component, a first positioning component 108, a second positioning component 110, and a button cell battery 114 in accordance with the disclosure.

An example of a wearable device in accordance with the disclosure is shown in FIG. 1. In this example, the wearable device 104 is illustrated as a necklet 104 that can be worn by a person. The wearable device 104 may include a sound sensor 106, a temperature sensor 120, a data transmission component 112, a first positioning component 108, a second positioning component 110, and a button cell battery 114. In other embodiments not shown here, the wearable device 104 may be removably attached to a clothing 102 worn by a person. In some other examples, the wearable device may be in some other forms so long as it can be worn by a person. For example, the wearable device 104 may be a pacifier for a baby, or a watch that can be worn by a person. This is not intended to be limiting. It should be understood while "baby" is used sometimes in this disclosure, the age of the person that can wear the wearable device 104 is not intended to be limiting. It is contemplated that the wearable device in accordance with the disclosure may be worn by an adolescent or an adult for detecting, indicating, and/or addressing abnormal breathing by the adolescent or the adult. For example, wearable device 104 may be worn by an adult patient with breathing disease.

Depending on the needs, the wearable device 104 may include various kinds and/or numbers of sensors, such as, sound sensor, temperature sensor, heartbeat sensor, pulse sensor, blood pressure sensor, and/or other sensors to detect other body signals. The wearable device 104 may include only a sound sensor 106, or only a temperature sensor 120, or a sound sensor 106 plus a temperature sensor 120, or an integrated sound and temperature sensor.

As still shown, the wearable device 104 may include a sound sensor 106 configured to collect breathing sounds produced by the person wearing the wearable device 104. For collecting the breathing sounds of the person, a few factors need to be taken into account. First, the sound sensor 106 may not be very "sensitive" in picking up sound signals except for those produced by the person within close range where the sound sensor 106 is placed. In this way, noises may not be collected or may be reduced. Second, the sound sensor 106 may be connected to a power source such as batteries in order for it to be powered and running. In embodiments, due to hazards that may be associated with batteries, especially to a newborn, selection of the batteries needs extra care. Preferably, a button cell battery 114 as shown may be used for such a power source. In any case, the sound sensor 106 may be coupled to a wire that is capable for transmitting analog signals, or coupled to a wireless data transmission component 112 for transmitting analog signals.

As still shown, the wearable device 104 may include a temperature sensor 120 configured to collect temperature signals produced by the person wearing the wearable device 104. The temperature sensor 120 may be placed in direct contact with skin of the person, for example, be placed under armpit of the person. Similar as the sound sensor, the temperature sensor 120 may be connected to a button cell battery 114 in order for it to be powered and running. In any case, the temperature sensor 120 may be coupled to a wire that is capable for transmitting analog signals, or coupled to a wireless data transmission component 112 for transmitting analog signals.

In some embodiments, the wearable device 104 may also include a wireless or wired data transmission component 112 that can transmit the sound signals collected by sound sensor 106 to a data analysis device 116. The wireless transmission component may employ any suitable wireless transmission technology such as Bluetooth, Near Field Communication (NFC), low radio frequency, WiFi and/or any other wireless technology. In embodiments, the data transmission component 112 may be powered by the same battery source 114 that powers the sound sensor 106 as shown.

In some embodiments, the wearable device 104 may also include a data analysis device 116. The data analysis device 116 may be integrated into the wearable device. However, this is not intended to be limiting. In some other embodiments, for reducing the size and weight of the wearable device in consideration of comfort, the data analysis device 116 may be included in a separate device. For example, the data analysis device 116 may be included in or provided by a desktop computer, a laptop computer, a smart phone, a tablet device, a medical device, or a server that is paired with wearable device 104 via wired or wireless link. Although not shown, the data analysis device 116 may include a communication module configured to communicate with wearable device 104 and/or a monitoring device 118 associated with a care-giver (e.g., a parent or a nurse). As mentioned above, the communication module included in the data analysis device may employ any suitable wireless communication technology such as Bluetooth, NFC, low radio frequency or WiFi.

Figure 3A:
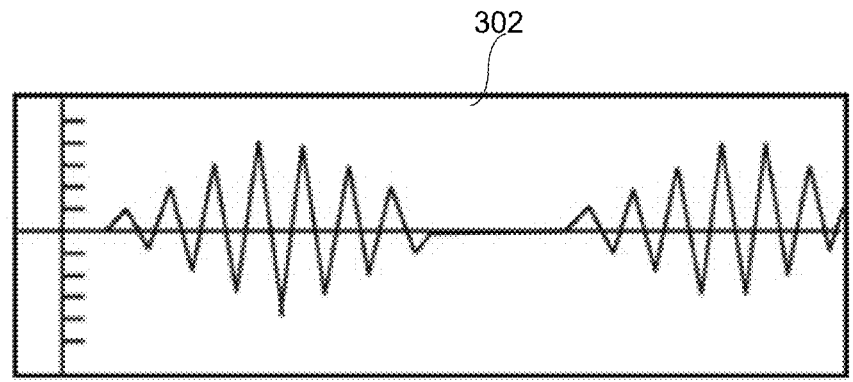
FIG. 3A illustrates one example of a current breathing pattern that can be stored in the system shown in FIG. 2.
Figure 6:
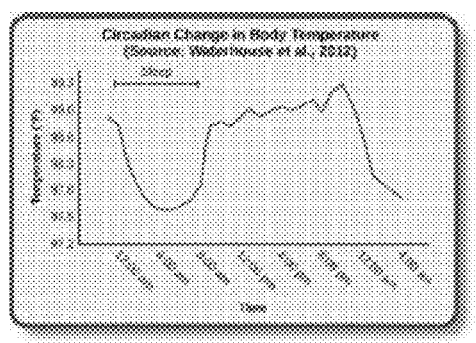
FIG. 6 illustrates one example of a current temperature pattern, one example of normal temperature pattern and four examples of abnormal temperature pattern that can be stored in the system shown in FIG. 5.
Figure 6:
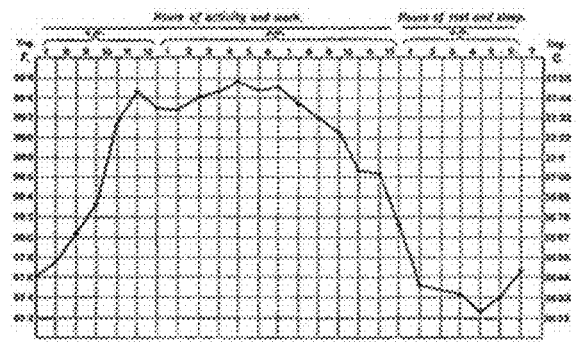
Figure 6:
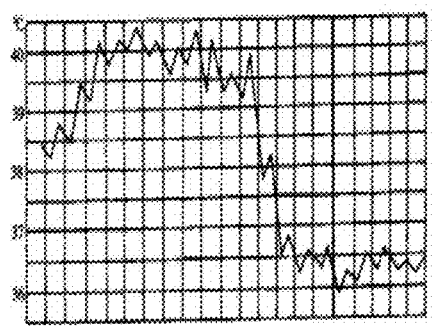
Figure 6:
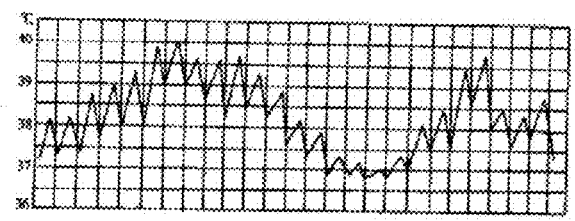
Figure 6:
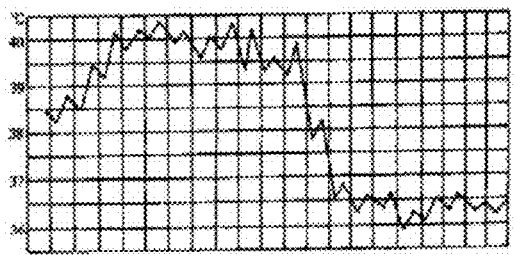
Figure 6:
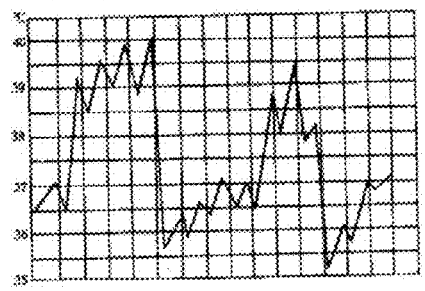

The data analysis device 116 can be configured to process the body signals received from the sensor. As mentioned above, the wearable device 104 may include a data transmission component 112 configured to transmit body signals collected by the sensor(s) to the data analysis device 116. In some embodiments, the transmission of the body signals may be via Bluetooth, NFC, low radio frequency or WiFi. In any case, after receiving the signals collected by the sensor, the data analysis device 116 may generate a current pattern based on the received signals. For example, the current pattern may indicate functioning by the person in the last 5 seconds. This current pattern may be continuously updated as the signals of the person are continuously received from sensor. Generating the current pattern by data analysis device 116 may include transcribing analog waveforms based on the signals received from the sensor. FIG. 3A illustrates one example of a current breathing pattern 302 that may be generated by the data analysis device 116. FIG. 6 illustrates one example of a current body temperature pattern 602 that may be generated by the data analysis device 116. Of course, the current pattern generated by the data analysis device 116 may be stored digitally in a data storage component associated with the data analysis device 116.

Figure 3B:
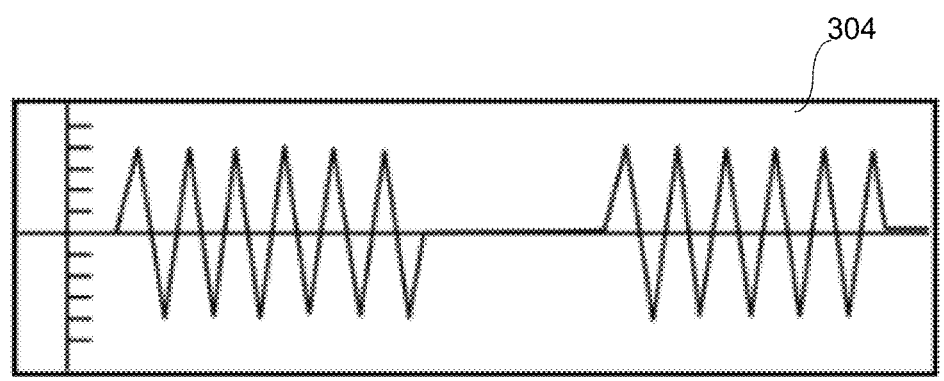
FIG. 3B illustrates two examples of normal breathing patterns that can be stored in the system shown in FIG. 2.
Figure 3B:
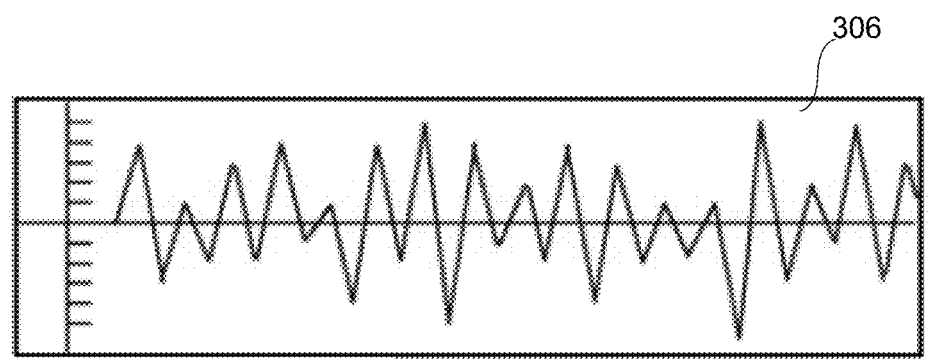

As the current pattern is being generated, the data analysis device 116 may be configured to compare the current pattern with one or more predetermined normal patterns for the person. The one or more predetermined normal patterns may be collected by a doctor, a nurse or the care-giver when the person is known to be functioning normally. In some embodiments, the one or more normal patterns of the person may be collected using the sensor and the data analysis device 116 in a recoding mode. FIG. 3B illustrates a couple of normal breathing patterns, i.e., 304 and 306 that can be collected. FIG. 604 in FIG. 6 illustrates a normal temperature pattern that can be collected. These normal patterns can be stored in the data storage component associated with the data analysis device 116 and retrieved from the data storage component to enable the data analysis device 116 to compare the current patterns to them.

In some embodiments, instead of or in addition to the predetermined normal patterns, one or more abnormal patterns may be stored in the data storage component associated with data analysis device. Such abnormal patterns may be collected from persons that were known to have certain ill conditions, or may be simulated by a doctor to indicate abnormal function that can be had by a person.

The pattern comparison by data analysis device 116 may involve fitting the current pattern to the one or more predetermined normal pattern, such as 304, 306 or 604 as shown. The comparison can further include determining whether the current normal pattern is conforming to the one or more predetermined normal patterns. In some embodiments, such conformance may be determined by data analysis device 116 when functioning by the person as indicated by the current pattern falls within a certain threshold with respect to the one or more predetermined normal patterns. It should be understood that a perfect match of the patterns for determining the current functioning by the person is not necessary. In certain embodiments, the data analysis device 116 may be configured with such a threshold for determining the pattern conformance.

In some embodiments, the data analysis device 116 may be configured to compare the current pattern to the one or more abnormal patterns mentioned above. In those embodiments, the data analysis device 116 may be configured to determine whether the current pattern is conforming to one of the one or more abnormal patterns. In some embodiments, the data analysis device 116 may be configured to first compare the current pattern with the one or more abnormal patterns to determine whether the current pattern conforms to one of the abnormal patterns. In response to a determination that such a conformance is found, the data analysis device 116 may be configured to generate a signal indicating that the person is functioning abnormally conforming to the known abnormal functioning pattern. In response to a determination that such a conformance is not found, the data analysis device 116 may be configured to further compare the current pattern with the one or more predetermined normal functioning patterns and to determine whether the current pattern conforms to the one or more predetermined normal functioning pattern. In response to such a conformance is not found, the data analysis device 116 may generate a signal indicating that the person is not functioning normally but is not functioning in a way to cause a known ill condition.

The data analysis device 116 can be configured to generate an alert instruction indicating the person is functioning abnormally in response to the abnormal functioning pattern by the person is detected by data analysis device 116. The alert instruction generated by the data analysis device 116 may include information indicating a timestamp when the person was first detected to be functioning abnormally, how long the person was detected to have been functioning abnormally, a known abnormal functioning pattern indicating a corresponding ill condition (if detected by data analysis device 116 as described above), and/or any other information.

The alert instruction generated by the data analysis device 116 can be transmitted to a monitoring device 118 as shown in FIG. 1. In some embodiments, the monitoring device 118 may include a smart phone, a tablet device, a laptop or any other portable computing device associated with a care-giver of the person so that the care-giver can be notified of the abnormal functioning timely. In other embodiments, the monitoring device 118 may include a medical device associated with medical person in medical organization, or an alert device associated with emergency aid persons so that the medical person or emergency aid person can be notified of the abnormal functioning timely.

The alert instruction from the data analysis device 116 can be implemented by the monitoring device 118 for generating a notification to notify the care-giver that the person is functioning abnormally. In some embodiments, the notification can be implemented to vibrate the monitoring device 118, to make a sound alert through the monitoring device 118, and/or to display a visual alert on the monitoring device 118. For example, when the notification indicates that continuous unknown abnormal functioning pattern by the person is detected and one or more vibrations or sound alert have been made through the monitoring device 118, a very loud and continuous sound alert may be generated to alert the care-giver. This may be desired because such a situation may indicate the care-giver is not aware the person is functioning abnormally. The visual alert may include information indicating various aspects regarding the abnormal functioning pattern by the person as described above. This can help the care-giver to quickly gain knowledge of the abnormal functioning by the person. As another example, the visual alert may be flashing or displaying an alert color or figure on the monitoring device 118.

In some embodiments, the wearable device 104 may also include a first positioning component 108 to locate position of the wearable device 104 in a first (large) area; and/or a second positioning component 110 to locate position of the wearable device 104 in a second (small) area. The first positioning component 108 can be a GPS (global positioning system) component to locate the wearable device 104 in a large are. The second positioning component 110 can be one or combination of the following: a blue tooth component, an infrared component, an laser component, a RFID (radio frequency identification) component, a Wi-Fi component, a ZigBee component, or an UWB (Ultra Wide Band) component. Through combination of the two positioning components 108 and 110 in large and small area, the care-giver can efficiently and accurately locate the person wearing the wearable device when the monitoring device generates an alert notification. As another example, when the wearable device is removed from the person or lost, the care-giver can also efficiently and accurately locate the wearable device through combination of the two positioning components.

Figure 2:
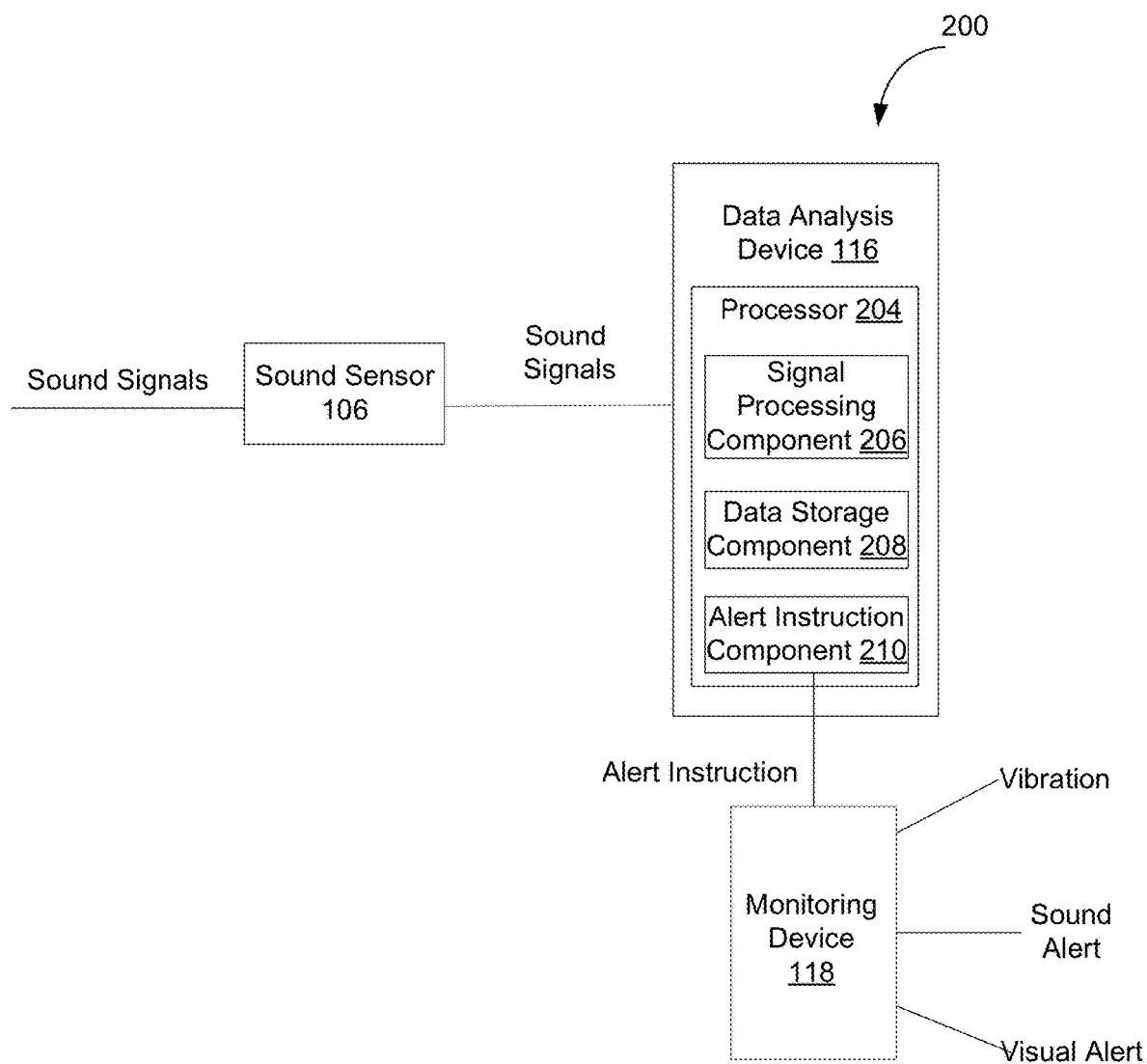
FIG. 2 illustrates one example of a system configured to monitor and address the abnormal breathing pattern of a person wearing the wearable device shown in FIG. 1.

With an example of wearable device 104 in accordance with the disclosure being generally described, attention is now directed to FIG. 2, where an example of a system 200 configured to monitor abnormal breathing pattern of the person wearing the wearable device 104 shown in FIG. 1 and to notify such to a care-giver is shown. It will be described with reference to FIG. 1. As shown, the system 200 may include a data analysis device 116 comprising one or more of a processor 204. In any case, as shown, the processor 204 may be configured to have program components including a signal processing component 206, an alert instruction component 210, a data storage component 208, and/or any other program components.

The signal processing component 206 can be configured to process the breathing sound signals received from the sound sensor 106. In any case, after receiving the breathing sound signals collected by the sound sensor 106, the signal processing component 206 may generate a current breathing pattern based on the received breathing sound signals. Generating the current breathing pattern by signal processing component 206 may include transcribing analog waveforms based on the volume of the sound signals received from the sound sensor 106. FIG. 3A illustrates one example of a current breathing pattern 302 that may be generated by the signal processing component 206. Of course, the breathing pattern 302 generated by the signal processing component 206 may be stored digitally in a data storage component 208 associated with the data analysis device 116.

As the current breathing pattern 302 is being generated, the signal processing component 206 may be configured to compare the current breathing pattern 302 with one or more predetermined normal breathing patterns for the person. FIG. 3B illustrates a couple of normal breathing patterns, i.e., 304 and 306 that can be collected. These breathing patterns can be stored in the data storage component 208 associated with the data analysis device 202 and retrieved from the data storage component 208 to enable the signal processing component 206 to compare the current breathing pattern 302 to them.

In some embodiments, instead of or in addition to the predetermined normal breathing patterns, one or more abnormal breathing patterns may be stored in the data storage component 208 associated with data analysis device.

The breathing pattern comparison by signal processing component 206 may involve fitting the current breathing pattern 302 to the one or more predetermined normal breathing pattern, such as 304 and 306 as shown. The comparison can further include determining whether the current normal breathing pattern is conforming to the one or more predetermined normal breath patterns. In some embodiments, such conformance may be determined by signal processing component 206 when a frequency of high low tidal volume of the breathing by the person as indicated by the current breathing pattern 302 falls within a certain threshold with respect to the one or more predetermined normal breathing patterns. In certain embodiments, the signal processing component 206 may be configured with such a threshold for determining the pattern conformance.

In some embodiments, the signal processing component 206 may be configured to compare the current breathing pattern 302 to the one or more abnormal breathing patterns mentioned above. In those embodiments, the signal processing component 206 may be configured to determine whether the current breathing pattern 302 is conforming to one of the one or more abnormal breathing patterns. In some embodiments, the signal processing component 206 may be configured to first compare the current breathing pattern 302 with the one or more abnormal breathing patterns to determine whether the current breath pattern 302 conforms to one of the abnormal breathing patterns. In response to a determination that such a conformance is found, the signal processing component 206 may be configured to generate a signal indicating that the person is breathing abnormally conforming to the known abnormal breathing pattern. In response to a determination that such a conformance is not found, the signal processing component 206 may be configured to further compare the current breathing pattern 302 with the one or more predetermined normal breathing patterns and to determine whether the current breathing pattern 302 conforms to the one or more predetermined normal breathing pattern. In response to such a conformance is not found, the signal processing component 206 may generate a signal indicating that the person is not breathing normally but is not breathing in a way to cause a known respiratory condition.

The alert instruction component 210 can be configured to generate an alert instruction indicating the person is breathing abnormally in response to the abnormal breathing pattern by the person is detected by signal processing component 206. The alert instruction generated by the alert instruction component 210 may include information indicating a timestamp when the person was first detected to be breathing abnormally, how long the person was detected to have been breathing abnormally, a known abnormal breathing pattern indicating a corresponding respiration condition (if detected by signal processing component 206 as described above), and/or any other information. The alert instruction generated by the alert instruction component 210 can be transmitted to a monitoring device 118, and to generate a notification for notifying a care-giver that the person is breathing abnormally, as described above.

Figure 4:
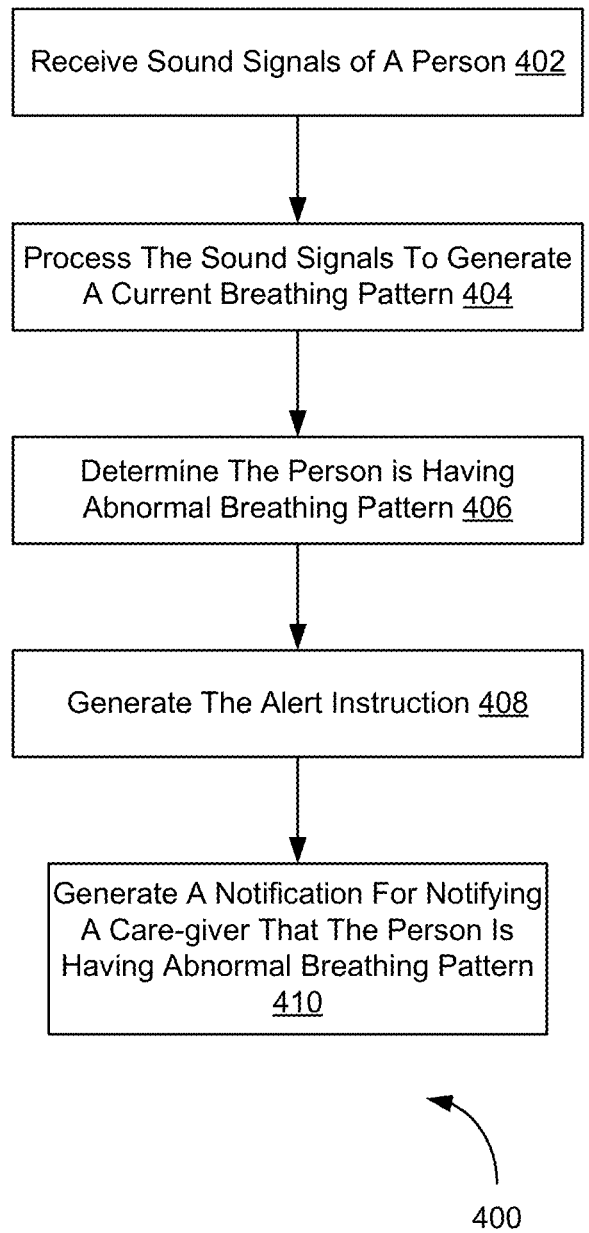
FIG. 4 illustrates one exemplary method for generating an alert instruction by the data analysis device shown in FIG. 1 and for notifying the care-giver of the abnormal breathing.

Attention is now directed to FIG. 4 which illustrates an exemplary method 400 for monitoring abnormal breathing pattern of the person wearing the wearable device 104 shown in FIG. 1 and for notifying of such to a care-giver. The particular series of processing steps depicted in FIG. 4 is not intended to be limiting. It is appreciated that the processing steps may be performed in an order different from that depicted in FIG. 4 and that not all the steps depicted in FIG. 4 need be performed. In certain embodiments, the method 400 may be implemented by a computer system, such as the computer system shown in FIG. 5.

In some embodiments, the method depicted in method 400 may be implemented in one or more data analysis devices (e.g., a digital processor, an analog processor, a digital circuit designed to process information, an analog circuit designed to process information, a state machine, and/or other mechanisms for electronically processing information). The one or more data analysis devices may include one or more devices executing some or all of the operations of method 400 in response to instructions stored electronically on an electronic storage medium. The one or more data analysis devices may include one or more devices configured through hardware, firmware, and/or software to be specifically designed for execution of one or more of the operations of method 400.

At 402, sound signals of a person can be received. As described and illustrated herein, a wearable device such as the wearable device 104 shown in FIG. 1 can be worn by the person. The wearable device can include a sound sensor, a data transmission component, a first positioning component, a second positioning component and/or any other components. The sound sensor can be attached to the wearable device such that it can collect breathing sounds of the person. The sound signals collected by the sound sensor can be received at 402 at a data analysis device paired with wearable device 104 via Bluetooth. In some embodiments, operations involved in 402 can be implemented by a signal processing component the same as or substantially similar to signal processing component 206 described and illustrated herein.

At 404, the sound signals received at 402 can be processed to generate a current breathing pattern of the person. The current breathing pattern generated at 404 may indicate breathing by the person in the last a few seconds. This current breathing pattern may be continuously updated as the sound signals are continuously received at 402. Generating the current breathing pattern at 404 may include transcribing analog waveforms based on the volume of the sound signals received at 402. FIG. 3A illustrates one example of a current breathing pattern 302 that may be generated at 404. In some embodiments, operations involved in 404 can be implemented by a signal processing component the same as or substantially similar to signal processing component 206 described and illustrated herein.

At 406, a determination that the person is breathing abnormally may be made. The determination made at 406 may involve comparing the current breathing pattern generated at 404 with one or more predetermined normal breathing patterns of the person. The one or more predetermined normal breathing patterns of the person may be collected by a doctor, a nurse or the care-giver when the person is known to be breathing normally. In some embodiments, the one or more normal breathing patterns of the person may be collected using the sound sensor 106 and the data analysis device 116 in a recoding mode. FIG. 3B illustrates a couple of normal breathing patterns, i.e., 304 and 306 that can be collected. The comparison of the breathing patterns can include determining whether the current normal breathing pattern generated at 404 is conforming to the one or more predetermined normal breath patterns. Such conformance may be found when a frequency of high low tidal volume of the breathing by the person as indicated by the current breathing pattern generated at 404 falls within a certain threshold with respect to the one or more predetermined normal breathing patterns.

In some embodiments, the determination made at 406 may involve comparing the current breathing pattern generated at 404 with one or more predetermined abnormal breathing patterns of the person. The abnormal breathing patterns of the person may be collected from people that were known to have certain respiratory conditions, or may be simulated by a doctor to indicate abnormal breathing that can be had by a person. In some embodiments, the determination at 406 may first involve comparing the current breathing pattern generated at 404 with the one or more abnormal breathing patterns to determine whether the current breath pattern conforms to one of the abnormal breathing patterns. In response to a determination that such a conformance is found, a determination indicating that the person is breathing abnormally conforming to the known abnormal breathing pattern can be made. In response to a determination that such a conformance is not found, the current breathing pattern generated at 404 can be compared with the one or more predetermined normal breathing patterns for determining whether the current breathing pattern conforms to the one or more predetermined normal breathing pattern. In response to such a conformance is not found, a determination that the person is generally breathing abnormally (i.e., breathing abnormally in an unknown way) can be made. In some embodiments, operations involved in 406 can be implemented by a signal processing component the same as or substantially similar to signal processing component 206 described and illustrated herein.

At 408, an alert instruction for a monitoring device to generate a notification for notifying a care-giver that the person is breathing abnormally can be made in response to the determination made at 406. For example, as described above, a determination indicating that the person is breathing abnormally in a known incorrect breathing pattern may be made at 406. The alert instruction generated at 408 may include information indicating a timestamp when the person was first detected to be breathing abnormally, how long the person was detected to have been breathing abnormally, a known abnormal breathing pattern indicating a corresponding respiration condition (if determined at 406 as described above), and/or any other information. In some embodiments, the alert instruction generated at 408 may include information indicating a number of times due to continuous detection of abnormal breathing by the person. In response to such a determination, the alert instruction may be generated at 408 to enable the monitoring device to generate a notification. The alert instruction generated at 408 can be transmitted wirelessly to the monitoring device held by the care-giver. Upon receiving such an alert instruction, the monitoring device may generate a notification for notifying a care-giver that the person is breathing abnormally. In some embodiments, operations involved in 408 can be implemented by inflation component the same as or substantially similar to a inflation component 208 described and illustrated herein.

At 410, a notification for notifying a care-giver that the person is breathing abnormally can be generated by the monitoring device in response to determination made at 406. The alert instruction generated at 408 can be transmitted to a monitoring device associated with the care-giver, such as the monitoring device 118 shown in FIG. 2. The notification can be implemented on such a monitoring device to notify the care-giver that the person is breathing abnormally. In some embodiments, the notification can be implemented to vibrate the monitoring device, to make a sound alert through the monitoring device, and/or to display a visual alert on the monitoring device. In some embodiments, operations involved in 410 can be implemented by an alert instruction component the same as or substantially similar to an alert instruction component 210 described and illustrated herein.

For temperature monitoring, temperature control (thermoregulation) is part of a homeostatic mechanism that keeps the organism at optimum operating temperature, as the temperature affects the rate of chemical reactions. In humans, the average internal temperature is 37.0° C. (98.6° F.), though it varies among individuals. However, no person always has exactly the same temperature at every moment of the day. Temperatures cycle regularly up and down through the day, as controlled by the person's circadian rhythm. The lowest temperature occurs about two hours before the person normally wakes up. Additionally, temperatures change according to activities and external factors. In addition to varying throughout the day, normal body temperature may also differ as much as 0.5° C. (0.9° F.) from one day to the next, so that the highest or lowest temperatures on one day will not always exactly match the highest or lowest temperatures on the next day. Normal human body temperature varies slightly from person to person and by the time of day. Consequently, each type of measurement has a range of normal temperatures. The range for normal human body temperatures, taken orally, is 36.8±0.5° C. (98.2±0.9° F.). This means that any oral temperature between 36.3 and 37.3° C. (97.3 and 99.1° F.) is likely to be normal. The normal human body temperature is often stated as 36.5-37.5° C. (97.7-99.5° F.). In adults a review of the literature has found a wider range of 33.2-38.2° C. (91.8-100.8° F.) for normal temperatures, depending on the gender and location measured. A normal temperature in babies and children is about 36.4° C. (97.5° F.), but this can vary slightly. A fever for babies and children is usually considered to be a temperature of 38° C. (100.4° F.) or above. FIG. 6 illustrates some temperature pattern of a person, wherein 602 illustrates an example of a current temperature pattern of a person in one day, 604 illustrates an example of a normal temperature pattern of a person in one day. Some exemplary abnormal temperature patterns are illustrated in 606, 608, 610 and 612.

Figure 5:
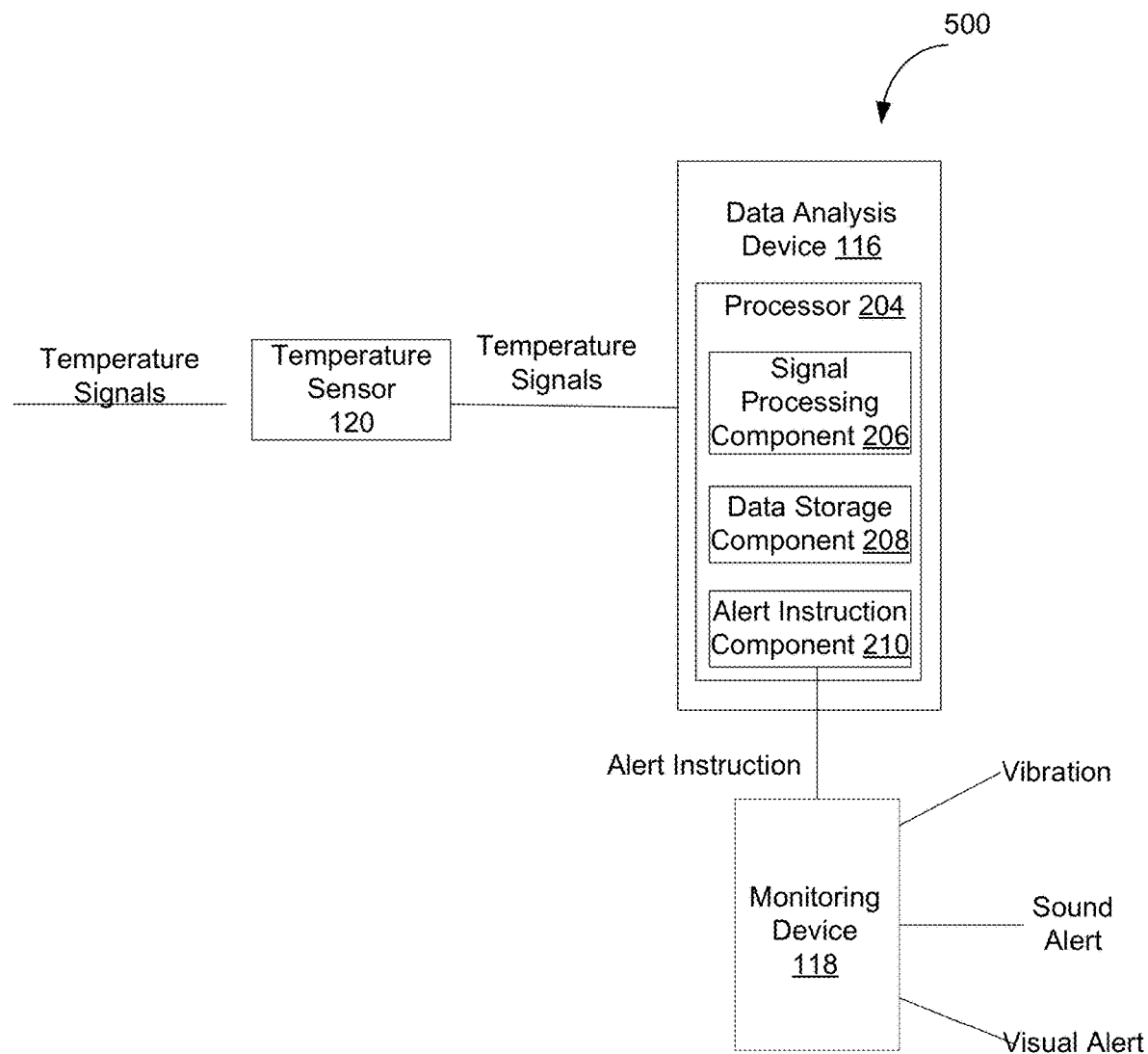
FIG. 5 illustrates one example of a system configured to monitor and address the abnormal temperature pattern of a person wearing the wearable device shown in FIG. 1.

FIG. 5 illustrates an example of a system 500 configured to monitor abnormal temperature pattern of the person wearing the wearable device 104 shown in FIG. 1 and to notify such to a care-giver is shown. It will be described with reference to FIG. 1. As shown, the system 500 may include a data analysis device 116 comprising one or more of a processor 204. In any case, as shown, the processor 204 may be configured to have program components including a signal processing component 206, an alert instruction component 210, a data storage component 208, and/or any other program components. Detailed configuration and operation of the system 500 may be similar as system 200 in FIG. 2.

Figure 7:
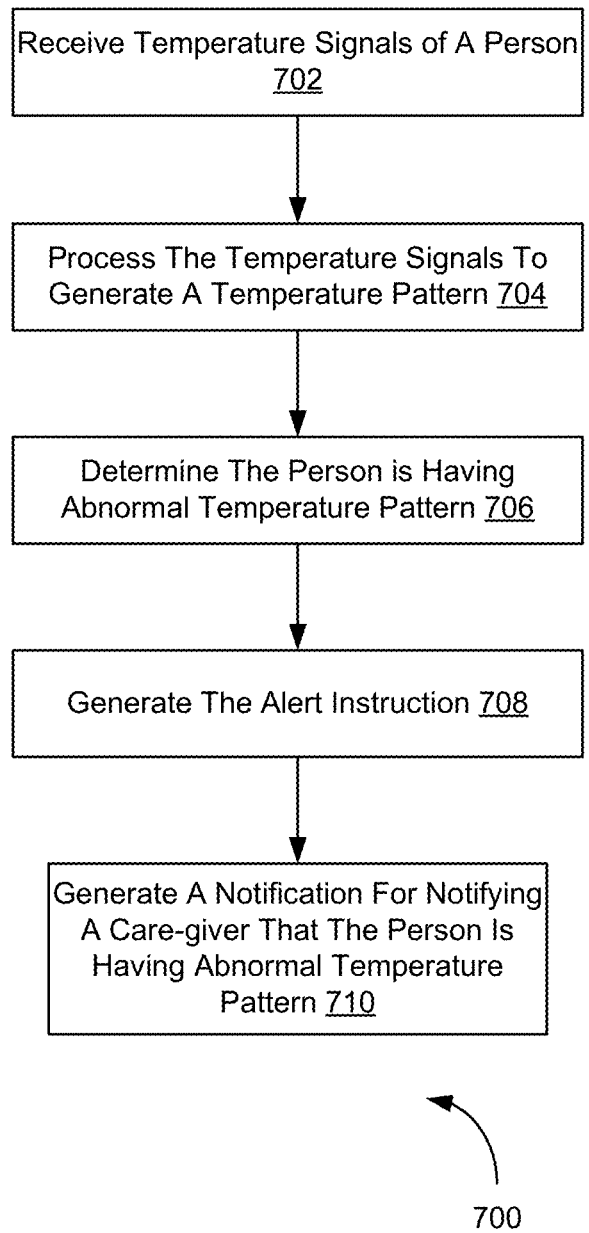
FIG. 7 illustrates one exemplary method for generating an alert instruction by the data analysis device shown in FIG. 1 and for notifying the care-giver of the abnormal temperature.

Attention is now directed to FIG. 7 which illustrates an exemplary method 700 for monitoring abnormal temperature pattern of the person wearing the wearable device 104 shown in FIG. 1 and for notifying of such to a care-giver. The particular series of processing steps depicted in FIG. 7 is not intended to be limiting. It is appreciated that the processing steps may be performed in an order different from that depicted in FIG. 7 and that not all the steps depicted in FIG. 7 need be performed. In certain embodiments, the method 700 may be implemented by a computer system, such as the computer system shown in FIG. 5. Detailed configuration and operation of the method 700 may be similar as method 400 in FIG. 4.

Figure 8:
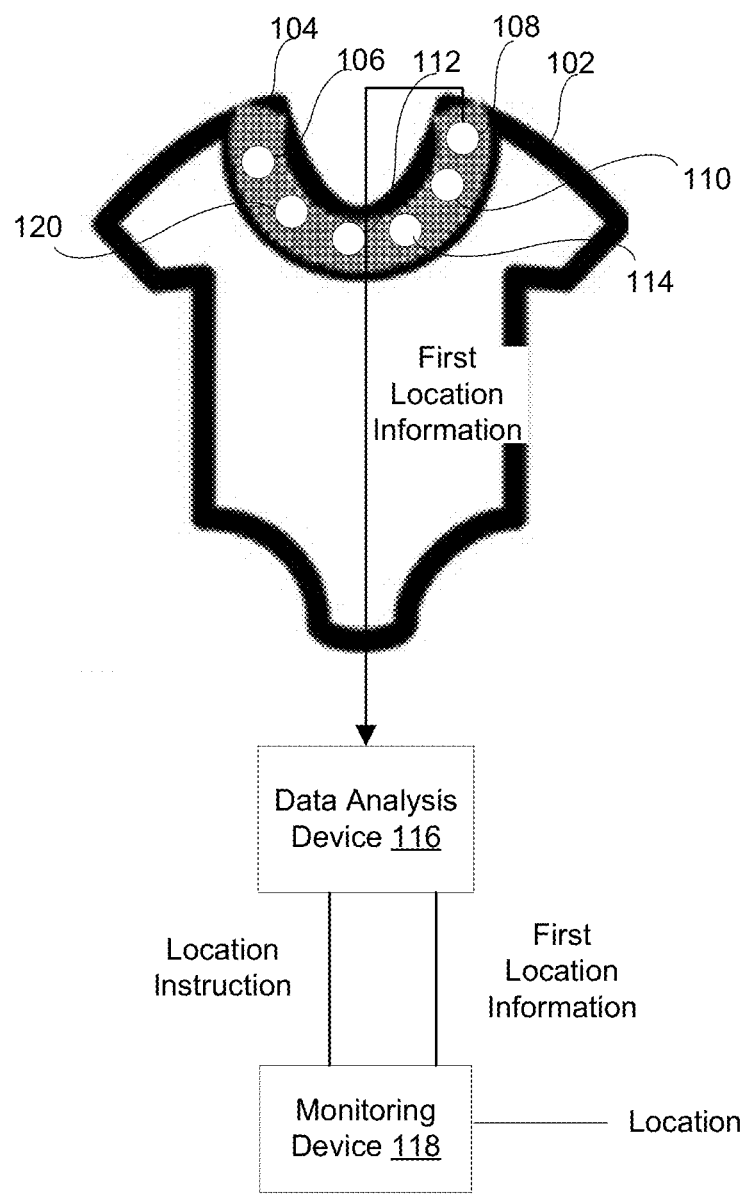
FIG. 8 illustrates one example of a wearable device that has a first positioning component to locate the wearable device in a first area.

In some embodiments, the wearable device 104 may also include a first positioning component 108 to locate position of the wearable device 104 in a large area as shown by FIG. 8. The first positioning component 108 may include a typical GPS (global positioning system) receiver. Although not shown, the GPS receiver may include antenna to receive the location data of GPS satellites, microprocessor, and storage component to store data. The microprocessor may be configured to process the location data of GPS satellites, and to generate a first location information of the wearable device 104. The GPS receiver may be coupled to a wire that is capable for transmitting the first location information of the wearable device 104 to the data analysis device 116, or coupled to a wireless data transmission component 112 for transmitting the first location information of the wearable device 104 to the data analysis device 116. In some embodiments, the transmission of the location information may be via Bluetooth, NFC, low radio frequency or WiFi.

As shown in FIG. 2 or FIG. 5, the data analysis device 116 may include one or more of a processor 204, a signal processing component 206, an alert instruction component 210, a data storage component 208, and/or any other program components. The data analysis device 116 may transmit the first location information of the wearable device 104 to the monitoring device 118 through the alert instruction component 210. The monitoring device 118 can indicate the location of the wearable device 104 based on the first location information. When a notification that the person is functioning abnormally be made to a care-giver at 410 or 710, the care-giver can locate the person wearing the wearable device 104 through the location indicated by the monitoring device 118.

In some embodiments, the data analysis device 116 may store a plurality of the first location information of the wearable device for a period of time through the data storage component 208, for example, for last 5 minutes. This time period and the frequency that the first positioning component 108 generates the first location information can be set by the care-giver on the data analysis device 116 or the monitoring device 118. In certain condition, such that the wearable device is out of power, or the wearable device is lost, or the person wearing the wearable device is lost, or the location information signal is too weak due to remoteness, the data analysis device 116 may store the last received the first location information of the wearable device so that the care-giver can locate the person wearing the wearable device, and/or the wearable device. In some embodiments, the monitoring device 118 may transmit a location instruction to the data analysis device 116 to require the first location information of the wearable device.

By way of example, in some embodiment, the first positioning component 108 may be configured to obtain a current GPS location of the wearable device from time to time (e.g., every minute). The frequency of obtaining the current GPS location by the first positioning component 108 is not intended to be limited. In those examples, the first positioning component 108 may be configured to transmit the current GPS location to the data analysis device 116 for storage from time to time. However, this is also not intended to be limiting. It is understood that the first positioning component 108 may be configured to simply store historical GPS locations on the first positioning component 108, e.g., in a non-volatile memory of the first positioning component 108. In any case, the historical GPS data can be used later to locate the wearable device when an alert is received by the monitoring device 118.

Figure 9:
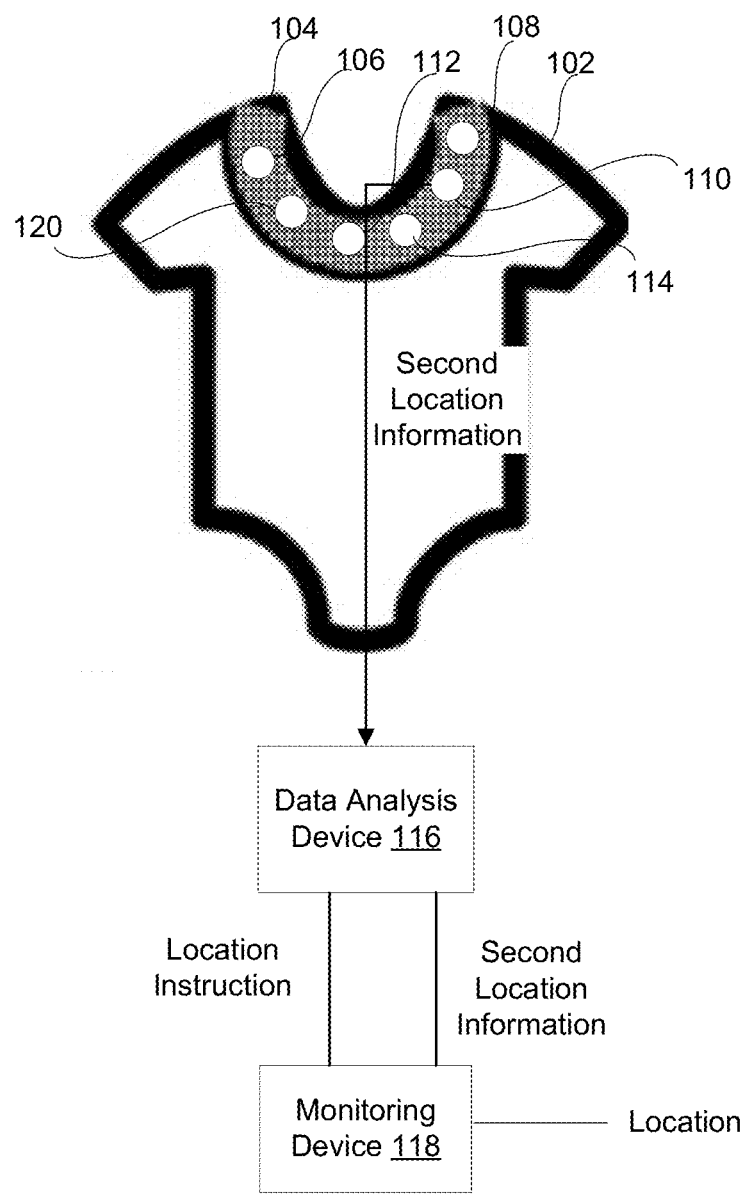
FIG. 9 illustrates one example of a wearable device that has a second positioning component to locate the wearable device in a second area.

For example, in response to receiving the alert instruction from the data analysis device 116, the monitoring device 118 may be configured to obtain the historical GPS data from the data analysis device 116 and/or from the wearable device 104. Of course, it is understood that GPS location may not be accurate enough to know where the wearable device 104 is within finer precision. For instance, the historical GPS data may only indicate that the wearable device 104 is located at a GPS location indicating a particular building, but it may not provide finer location information such as which floor and/or room the wearable device 104 is at the moment. For addressing this, in some embodiments, the wearable device 104 may also include a second positioning component 110 to locate position of the wearable device 104 with a finer precision than the first positioning component 108, as shown by FIG. 9.

For example, the second positioning device 110 may include a beacon component configured to consistently emit beacon signals at a certain frequency such that the beacon signals may be received within a preconfigured range. In that example, the second positioning device 110 may be activated-able upon an instruction or request indicating an identification associated with the beacon component. That is, at a low power mode, the beacon component may be configured to scan signals for such a request, and once the request is scanned, the second positioning device 110 may be activated to emit beacon signals.

Still in that example, once the GPS location is determined for the wearable device 104. The monitoring device 118 may be brought (e.g., physically) to the GPS location to locate the wearable device 104 (and hence a person or persons wearing the wearable device 104). Once at the GPS location of the wearable device 104, the monitoring device 118 may send signals requesting the second positioning device 110 to be activated. As mentioned above, the monitoring device may be configured to broadcast signals indicating the identification of the wearable device 104. Once the beacon signals from the second positioning device is received by the monitoring device 118, information related to beacon signals (e.g., its strength and direction) can be used by the monitoring device 118 to locate the wearable device 104.

However, it should be understood that the example provided above is not intended to be limiting. For example, it is contemplated that the monitoring device 118 may transmit relevant information regarding the wearable device 104 (such as its known GPS location and as well its identification) to a third party, such as a health care provider (e.g., emergency crew of a hospital). With such information, the health care provider can locate the wearable device 104 similarly as described above.

The second positioning component 110 can be one or combination of the following: a blue tooth component, an infrared component, an ultrasound component, a laser component, a RFID (radio frequency identification) component, a Wi-Fi component, a ZigBee component, or an UWB (Ultra Wide Band) component. The second positioning component 110 may be configured to generate a second location information of the wearable device 104. The second positioning component 110 may be coupled to a wire that is capable for transmitting the second location information of the wearable device 104 to the data analysis device 116, or coupled to a wireless data transmission component 112 for transmitting the second location information of the wearable device 104 to the data analysis device 116. In some embodiments, the transmission of the location information may be via Bluetooth, NFC, low radio frequency or WiFi.

As shown in FIG. 2 or FIG. 5, the data analysis device 116 may include one or more of a processor 204, a signal processing component 206, an alert instruction component 210, a data storage component 208, and/or any other program components. The data analysis device 116 may transmit the second location information of the wearable device 104 to the monitoring device 118 through the alert instruction component 210. The monitoring device 118 can indicate the location information of the wearable device 104 based on the second location information. When a notification that the person is functioning abnormally be made to a care-giver at 410 or 710, the care-giver can locate the person wearing the wearable device 104 through the location information indicated by the monitoring device 118.

In some embodiments, the data analysis device 116 may store a plurality of second location information of the wearable device for a period of time through the data storage component 208, for example, for last 5 minutes. This time period and the frequency that the second positioning component 110 generates the second location information can be set by the care-giver on the data analysis device 116 or the monitoring device 118. In certain condition, such that the wearable device is out of power, or the wearable device is lost, or the person wearing the wearable device is lost, or the location information signal is too weak due to remoteness, the data analysis device 116 may store the last received second location information of the wearable device so that the care-giver can locate the person wearing the wearable device, and/or the wearable device. In some embodiments, the monitoring device 118 may transmit a location instruction to the data analysis device 116 to require the second location information of the wearable device.

Figure 10:
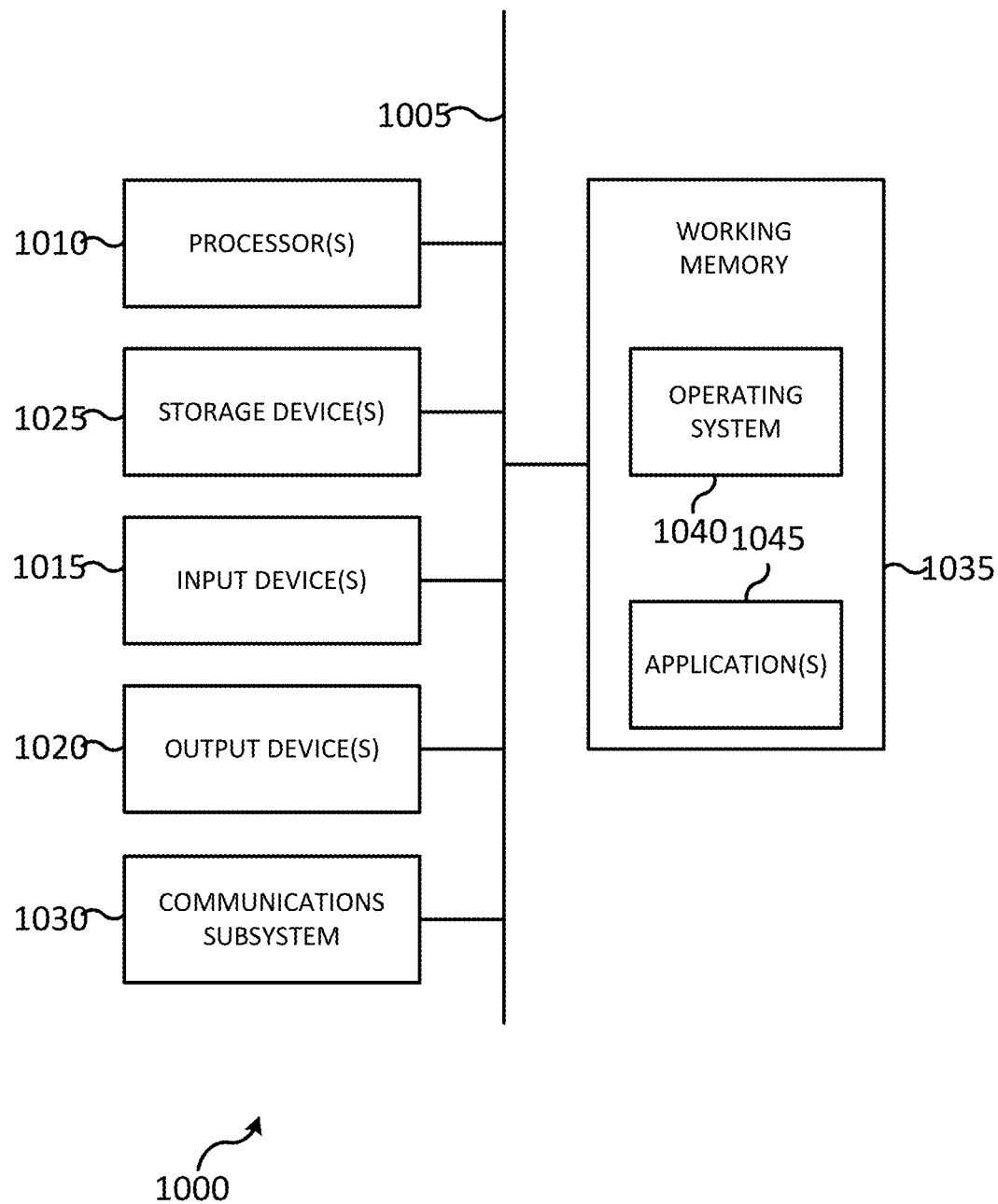
FIG. 10 illustrates one example of a computer system that can be used to implement various embodiments described and illustrated herein.

FIG. 10 illustrates a simplified computer system that can be used implement various embodiments described and illustrated herein. A computer system 1000 as illustrated in FIG. 10 may be incorporated into devices such as a portable electronic device, mobile phone, or other device as described herein. FIG. 10 provides a schematic illustration of one embodiment of a computer system 1000 that can perform some or all of the system provided by various embodiments. It should be noted that FIG. 10 is meant only to provide a generalized illustration of various components, any or all of which may be utilized as appropriate. FIG. 10, therefore, broadly illustrates how individual system elements may be implemented in a relatively separated or relatively more integrated manner.

The computer system 1000 is shown comprising hardware elements that can be electrically coupled via a bus 1005, or may otherwise be in communication, as appropriate. The hardware elements may include one or more processors 1010, including without limitation one or more general-purpose processors and/or one or more special-purpose processors such as digital signal processing chips, graphics acceleration processors, and/or the like; one or more input devices 1015, which can include without limitation a mouse, a keyboard, a camera, and/or the like; and one or more output devices 1020, which can include without limitation a display device, a printer, and/or the like.

The computer system 1000 may further include and/or be in communication with one or more non-transitory storage devices 1025, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable, and/or the like. Such storage devices may be configured to implement any appropriate data stores, including without limitation, various file systems, database structures, and/or the like.

The computer system 1000 might also include a communications subsystem 1030, which can include without limitation a modem, a network card (wireless or wired), an infrared communication device, a wireless communication device, and/or a chipset such as a Bluetooth™ device, an 1002.11 device, a WiFi device, a WiMax device, cellular communication facilities, etc., and/or the like. The communications subsystem 1030 may include one or more input and/or output communication interfaces to permit data to be exchanged with a network such as the network described below to name one example, other computer systems, television, and/or any other devices described herein. Depending on the desired functionality and/or other implementation concerns, a portable electronic device or similar device may communicate image and/or other information via the communications subsystem 1030. In other embodiments, a portable electronic device, e.g. the first electronic device, may be incorporated into the computer system 1000, e.g., an electronic device as an input device 1015. In some embodiments, the computer system 1000 will further comprise a working memory 1035, which can include a RAM or ROM device, as described above.

The computer system 1000 also can include software elements, shown as being currently located within the working memory 1035, including an operating system 1040, device drivers, executable libraries, and/or other code, such as one or more application programs 1045, which may comprise computer programs provided by various embodiments, and/or configure systems, provided by other embodiments, as described herein. Merely by way of example, one or more procedures described with respect to the system discussed above, such as those described in relation to FIG. 10, might be implemented as code and/or instructions executable by a computer and/or a processor within a computer; in an aspect, then, such code and/or instructions can be used to configure and/or adapt a general purpose computer or other device to perform one or more operations in accordance with the described system.

A set of these instructions and/or code may be stored on a non-transitory computer-readable storage medium, such as the storage device(s) 1025 described above. In some cases, the storage medium might be incorporated within a computer system, such as computer system 1000. In other embodiments, the storage medium might be separate from a computer system e.g., a removable medium, such as a compact disc, and/or provided in an installation package, such that the storage medium can be used to program, configure, and/or adapt a general purpose computer with the instructions/code stored thereon. These instructions might take the form of executable code, which is executable by the computer system 1000 and/or might take the form of source and/or installable code, which, upon compilation and/or installation on the computer system 1000 e.g., using any of a variety of generally available compilers, installation programs, compression/decompression utilities, etc., then takes the form of executable code.

It will be apparent to those skilled in the art that substantial variations may be made in accordance with specific requirements. For example, customized hardware might also be used, and/or particular elements might be implemented in hardware, software including portable software, such as applets, etc., or both. Further, connection to other computing devices such as network input/output devices may be employed.

As mentioned above, in one aspect, some embodiments may employ a computer system such as the computer system 1000 to perform system in accordance with various embodiments of the technology. According to a set of embodiments, some or all of the procedures of such methods are performed by the computer system 1000 in response to processor 1010 executing one or more sequences of one or more instructions, which might be incorporated into the operating system 1040 and/or other code, such as an application program 1045, contained in the working memory 1035. Such instructions may be read into the working memory 1035 from another computer-readable medium, such as one or more of the storage device(s) 1025. Merely by way of example, execution of the sequences of instructions contained in the working memory 1035 might cause the processor(s) 1010 to perform one or more procedures of the methods described herein. Additionally or alternatively, portions of the methods described herein may be executed through specialized hardware.

The terms "machine-readable medium" and "computer-readable medium," as used herein, refer to any medium that participates in providing data that causes a machine to operate in a specific fashion. In an embodiment implemented using the computer system 1000, various computer-readable media might be involved in providing instructions/code to processor(s) 1010 for execution and/or might be used to store and/or carry such instructions/code. In many embodiments, a computer-readable medium is a physical and/or tangible storage medium. Such a medium may take the form of a non-volatile media or volatile media. Non-volatile media include, for example, optical and/or magnetic disks, such as the storage device(s) 1025. Volatile media include, without limitation, dynamic memory, such as the working memory 1035.

Common forms of physical and/or tangible computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, EPROM, a FLASH-EPROM, any other memory chip or cartridge, or any other medium from which a computer can read instructions and/or code.

Various forms of computer-readable media may be involved in carrying one or more sequences of one or more instructions to the processor(s) 1010 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 1000.

The communications subsystem 1030 and/or components thereof generally will receive signals, and the bus 1005 then might carry the signals and/or the data, instructions, etc. carried by the signals to the working memory 1035, from which the processor(s) 1010 retrieves and executes the instructions. The instructions received by the working memory 1035 may optionally be stored on a non-transitory storage device 1025 either before or after execution by the processor(s) 1010.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of exemplary configurations including embodiments. However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a schematic flowchart or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the technology. Also, a number of steps may be undertaken before, during, or after the above elements are considered. Accordingly, the above description does not bind the scope of the claims.

As used herein and in the appended claims, the singular forms "a", "an", and "the" include plural references unless the context clearly dictates otherwise. Thus, for example, reference to "a sensor" includes a plurality of sensors, and reference to "the processor" includes reference to one or more processors and equivalents thereof known to those skilled in the art, and so forth. Ordinals such as "first sensor" and "second sensor" only mean they may be different. There is no specific sequence unless the context clearly dictates otherwise. Thus, for example, "first sensor" can be described as "second sensor", and vice versa.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

What is claimed is:

1. A wearable device, comprises:
    a first sensor configured to generate a first signal of a subject wearing the wearable device;
    a data transmission component configured to:
        receive the first signal generated by the first sensor; and
        transmit the first signal to a data analysis device to generate an alert instruction, wherein the data analysis device is configured to:
        generate a first pattern of the subject based on the first signal;
        determine whether the subject is functioning abnormally by comparing the first pattern with one or more predetermined abnormal patterns corresponding to one or more known conditions of the subject;
        in response to a determination that the first pattern conforms to the one or more abnormal patterns, determine that the subject is functioning abnormally, and generate a first alert instruction;
        transmit the first alert instruction to a monitoring device to generate a first notification for notifying a care-giver that the subject is functioning abnormally;
        in response to a determination that the first pattern doesn't conform to the one or more abnormal patterns, determine whether the subject is functioning abnormally by comparing the first pattern with one or more predetermined normal patterns of the subject;
        in response to a determination that the first pattern doesn't conform to the one or more normal patterns, determine that the subject is functioning abnormally, and generate a second alert instruction; and
        transmit the second alert instruction to the monitoring device to generate a second notification for notifying the care-giver that the subject is functioning abnormally; and
    a first positioning component configured to provide a first location information of the wearable device in a first area;
    wherein the first notification is more noticeable to the care-giver than the second notification.

2. The wearable device of claim 1, wherein the wearable device further comprises a second positioning component configured to provide a second location information of the wearable device in a second area.

3. The wearable device of claim 1, wherein the data analysis device further comprises:
    a data storage component configured to store the first pattern and the one or more predetermined abnormal patterns and normal patterns of the subject.

4. The wearable device of claim 1, wherein the data analysis device is further configured to determine whether the subject is having the one or more known conditions.

5. The wearable device of claim 1, wherein the first and second notification indicates at least one of when the abnormal functioning by the subject is first detected, and how long the subject is detected to be functioning abnormally.

6. The wearable device of claim 1, wherein the first and second notification includes at least one of vibrating the monitoring device associated with the care-giver, making a sound alert through the monitoring device associated with the care-giver, and displaying a visual alert on the monitoring device associated with the care-giver.

7. The wearable device of claim 1, wherein
    the first signal is a breathing sound or a breathing frequency of the subject.

8. The wearable device of claim 1, wherein
    the first signal is a temperature of the subject.

9. The wearable device of claim 1, wherein the first positioning component is a GPS (global positioning system) component.

10. The wearable device of claim 2, wherein the second positioning component is at least one of the following: a blue tooth component, an infrared component, an laser component, a RFID (radio frequency identification) component, a Wi-Fi component, a ZigBee component, or an UWB (Ultra Wide Band) component.

11. A method for monitoring a subject wearing a wearable device, the method comprising:
    generating, at the wearable device, a first signal, the first signal being generated by a first sensor of the wearable device;
    transmitting, at the wearable device, the first signal to a data analysis device to generate an alert instruction, the wearable device being coupled to the data analysis device;
    receiving, at the data analysis device, the first signal generated by the first sensor of the wearable device;
    generating, at the data analysis device, a first pattern of the subject based on the first signal;
    determining, at the data analysis device, whether the subject is functioning abnormally by comparing the first pattern with one or more predetermined abnormal patterns corresponding to one or more known conditions of the subject;
    in response to a determination that the first pattern conforms to the one or more abnormal patterns, determining, at the data analysis device, that the subject is functioning abnormally, and generating, at the data analysis device, a first alert instruction;
    transmitting, at the data analysis device, the first alert instruction to a monitoring device to generate a first notification for notifying a care-giver that the subject is functioning abnormally;
    in response to a determination that the first pattern doesn't conform to the one or more abnormal patterns, determining, at the data analysis device, whether the subject is functioning abnormally by comparing the first pattern with one or more predetermined normal patterns of the subject;

in response to a determination that the first pattern doesn't conform to the one or more normal patterns, determining, at the data analysis device, that the subject is functioning abnormally, and generating, at the data analysis device, a second alert instruction;

transmitting, at the data analysis device, the second alert instruction to the monitoring device to generate a second notification for notifying the care-giver that the subject is functioning abnormally; and in response to receiving the alert instruction, obtaining, at the monitoring device, a first location information regarding a location of the wearable device in a first area, the first location information being provided by a first positioning component of the wearable device;

wherein the first notification is more noticeable to the care-giver than the second notification.

12. The method of claim 11, wherein the method further comprises:

in response to receiving the alert instruction, obtaining, at the monitoring device, a second location information regarding the location of the wearable device in a second area, the second location information being provided by a second positioning component of the wearable device.

13. The method of claim 11, wherein the method further comprises:

storing, by a data storage component, the first pattern and the one or more predetermined abnormal patterns and normal patterns of the subject.

14. The method of claim 11, wherein the method further comprises:

determining, by the data analysis device, whether the subject is having the one or more known conditions.

15. The method of claim 11, wherein the first and second notification indicates at least one of when the abnormal functioning by the subject is first detected, and how long the subject is detected to be functioning abnormally.

16. The method of claim 11, wherein the first and second notification includes at least one of vibrating the monitoring device associated with the care-giver, making a sound alert through the monitoring device associated with the care-giver, and displaying a visual alert on the monitoring device associated with the care-giver.

17. The method of claim 11, wherein
the first signal is a breathing sound or a breathing frequency of the subject.

18. The method of claim 11, wherein
the first signal is a temperature of the subject.

* * * * *